United States Patent [19]

Voth et al.

[11] Patent Number: Plant 6,578

[45] Date of Patent: Jan. 31, 1989

[54] STRAWBERRY PLANT CALLED 'OSO GRANDE'

[75] Inventors: Victor Voth, Santa Ana; Royce S. Bringhurst, Davis, both of Calif.

[73] Assignee: Regents of the University of California, Berkeley, Calif.

[21] Appl. No.: 73,246

[22] Filed: Jul. 9, 1987

[51] Int. Cl.[4] ..... A01H 5/03

[52] U.S. Cl. ..... Plt./48

[58] Field of Search ..... Plt./48

*Primary Examiner*—Robert E. Bagwill

*Attorney, Agent, or Firm*—Townsend and Townsend

[57] ABSTRACT

A standard short-day type of strawberry plant characterized by its capability of exceptionally high yield of very large fruit, firmness and particularly fine flavor. The plant is of interest in all major strawberry fruit growing areas.

2 Drawing Sheets

DESCRIPTION

This invention relates to a new and distinctive short-day type strawberry cultivar designated as 'Oso Grande' (hereinafter to be called 'Oso' in this document) which is the result of a cross of 'Parker' (U.S. Plant Pat. No. 5263)×Cal 77.3-603 made in 1981. . The pedigree is as follows:

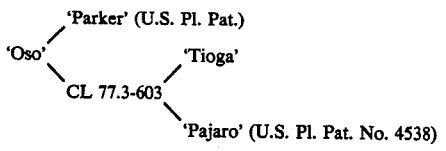

'Oso' first fruited at the South Coast Field Station in 1982 where it was selected and designated originally as Cal 81.43-603. It was tested later as advanced selection C43.

'Oso' has been propagated asexually by runners and has been tested at various University of California field stations and facilities and to a limited extent in a few growers' fields under Test Agreement.

In the photographs:

Figure 1:
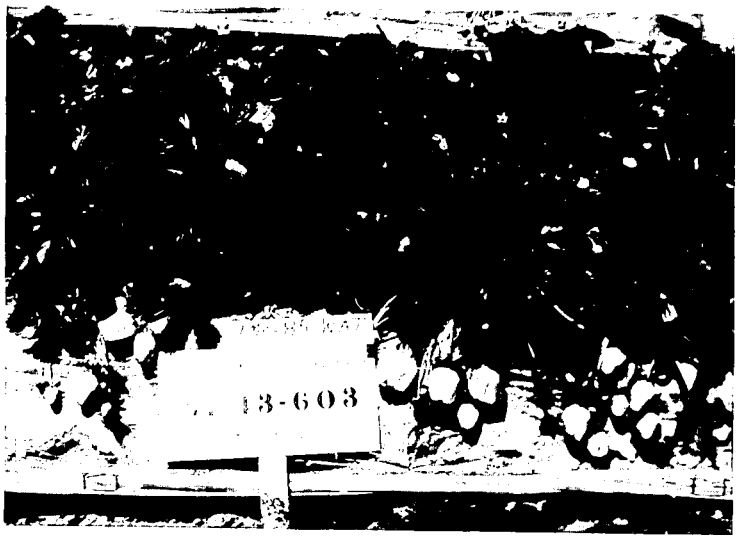
FIG. 1 shows typical growth, flowering and fruiting characteristics of the plant.
Figure 2:
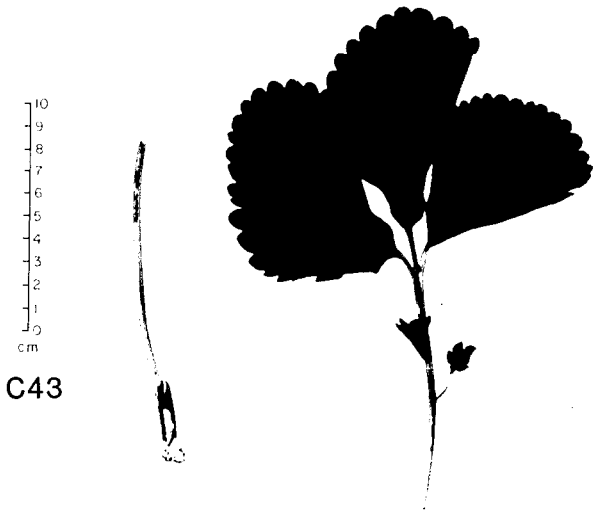
FIG. 2 shows a typical midfall mature leaf from a nursery plant.
Figure 3:
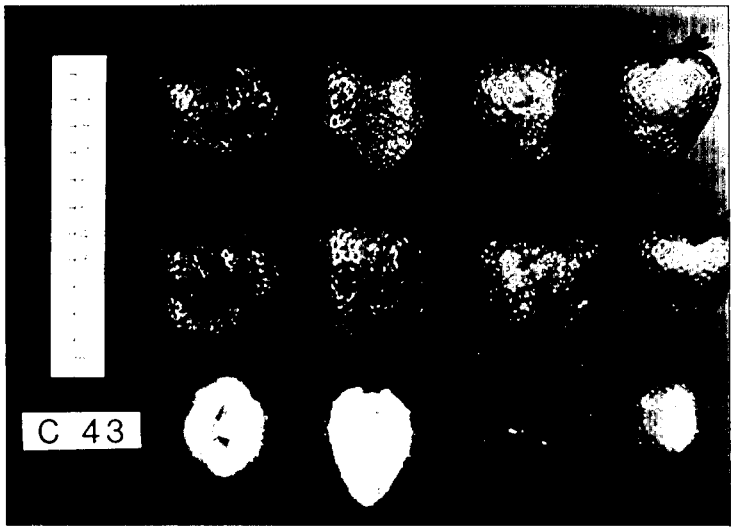
FIG. 3 shows individual representative early-season fruit with longitudinal and cross-sectional views.

'Oso' is medium early fruiting and has performed well in winter and summer planting experiments in south and central coastal California. It is later than 'Chandler', and both are later than 'Douglas'.

Plants and foliage: Leaf color and characteristics from late summer nursery plants of 'Oso' are compared with those of 'Douglas' *Pajaro', 'Chandler' and 'Parker' in Table* 1.

TABLE 1

| | OSO | DOUG-LAS | PA-JARO | CHAND-LER | PAR-KER |
|---|---|---|---|---|---|
| Color | 5GY 4/3 | 2.5GY 6/8 | 5GY 4/3 | 2.5GY 4/3 | 2.5GY 5.5 |
| Shape(length/width) | 1.07 | 1.28 | 1.14 | 1.16 | 1.20 |
| Base angle of terminal leaflet | 59° | 50° | 57° | 58° | 43° |
| Size of terminal | 77 | 83 | 85 | 77 | 84 |

TABLE 1-continued

| | OSO | DOUG-LAS | PA-JARO | CHAND-LER | PAR-KER |
|---|---|---|---|---|---|
| leaflets | | | | | |
| Serrations of terminal leaflets | 9.5 | 11.0 | 10.8 | 10.2 | 11.9 |
| Petiolule length (MM) | 16.7 | 12.0 | 15.3 | 9.2 | 11.9 |
| Petiole length (MM) | 235 | 241 | 145 | 177 | 198 |
| Bract leaflet position | .77 | .64 | .71 | .65 | .57 |

As shown above 'Oso' leaves are about the same color as those of 'Pajaro', darker and less yellow than 'Chandler'; similar to 'Douglas' and 'Parker'; (Munsell Color System—Nickerson Color Fan). Terminal leaflets are more nearly round than those of 'Douglas', 'Pajaro', 'Chandler' or 'Parker' as shown by length/-width measurements and half-blade terminal leaflet basal angles. 'Oso' terminal leaflets are about the same size as those of 'Chandler' and smaller than those of 'Douglas', 'Pajaro' and 'Parker' as determined by extracting the square root of the length×width measurements. Half terminal leaflet serration numbers are fewer than those of 'Douglas', 'Pajaro', 'Chandler' and 'Parker'. Petiolules (terminal leaflet stems) of 'Oso' are much longer than those 'Chandler', 'Parker' and 'Douglas' and somewhat longer than those of 'Pajaro'. 'Oso' plants are about the same size as those of 'Douglas'; larger than those of 'Parker', 'Chandler' or 'Pajaro' as indicated by petiole length. Bract leaflets occur on many of the petioles of 'Oso', somewhat higher up than those of 'Pajaro', 'Chandler' and 'Douglas' and considerably higher up than those of 'Parker', 77% vs 57%, respectively. Runner production is very good, comparable to that of 'Chandler'. Yellow "stripe" or "streak" occurs in the leaves occasionally (similar to 'Pajaro') and should be selected against in the nursery.

Isozymes in leaf extracts: 'Oso' has been characterized for three enzyme systems by starch gel electrophoresis: A. Phosphoglucoisomerase (PGI): B. Leucine amino peptidase (LAP); and C. Phosphoglucomutase (PGM). They compare with other standard short-day type California cultivars as follows:

TABLE 2

| | OSO | DOUGLAS | PAJARO | CHANDLER | PARKER |
|---|---|---|---|---|---|
| PGI | A2 | A3 | A4 | A1 | A4 |
| LAP | B3 | B3 | B3 | B3 | B3 |
| PGM | C2 | C1 | C1 | C1 | C2 |

'Oso' can thus be distinguished unambiguously from the five comparison cultivars by using only two enzyme systems (PGI and PGM). The 'Oso' pattern however, is identical to that of California day-neutral 'Selva' (U.S. Plant Pat. No.5,266).

Disease and pest reaction: 'Oso' is highly resistant to (tolerant of) the virus diseases common in California including "Mild Yellow Edge" and complexes involving it. It is quite susceptible to common leafspot (Ramularia), at least as susceptible as 'Chandler' or 'Pajaro', more susceptible than 'Douglas' or 'Parker'. 'Oso' is about equal to 'Chandler' or 'Pajaro' in sensitivity to two-spotted mite infestation, a little less sensitive than 'Parker' and 'Douglas'.

Flowering, fruiting, fruit and production characteristics: 'Oso' is a standard, facultative short-day type cultivar, subject to modification in fruiting response in California as influenced by day-length, growing temperature and chilling. Flowers, borne on relatively long peduncles are large and attractive with 5 to 7 petals and are completely self-fertile with ample pollen throughout the season. Pollination is generally good with minimal malformation. The fruit shape is blocky to wedgy medium conic and may be somewhat hollow. 'Oso' yield and midseason fruit and quality characteristics are compared with those of important short-day type California cultivars as grown under optimum conditions under the "hill" system in winter plantings at the University of California Strawberry Research Facility Watsonville in Table 3.

TABLE 3

| | OSO | DOUGLAS | PAJARO | CHANDLER | PARKER |
|---|---|---|---|---|---|
| Yield (GR/Plant) | 2202 | 1495 | 1060 | 1924 | 1587 |
| Size (GR/Fruit) | 27.6 | 27.5 | 24.8 | 24.1 | 25.1 |
| Firmness | 6.2 | 5.0 | 5.9 | 5.7 | 6.7 |
| Color | 7.5R4.5/11 | 6R4/12 | 5R4/12 | 5R4/12 | 7R4.5/13 |
| Ascorbic acid | 31.9 | 27.8 | 37.7 | 25.3 | 25.9 |
| Soluble solids | 7.7 | 7.8 | 7.7 | 7.8 | 7.7 |

'Oso' is capable of yielding as much or more than the highest yielding California cultivars including 'Chandler'. Fruit size averages as larger or larger than the largest fruited California cultivars, including 'Douglas'. 'Oso' fruit is very firm, almost equal to that of 'Parker', much firmer than 'Chandler' or 'Douglas' as measured by a penetrometer equipped with a "Hunter Force Gage" and it handles very well. The fruit skin color is similar to that of 'Parker' but less red than 'Chandler', 'Douglas' or 'Pajaro'. The finish is particularly bright and attractive. The flesh color is about the same as the skin but less intense with a distinctly lighter ring around the core. The achenes are medium sized (smaller than those of 'Douglas'), bright yellow and positioned about even with the skin surface. The calyx is medium to large sized, positioned from even with the base of the fruit to being borne on or short rather thick neck, somewhat reflexed. The ascorbic acid content ranges from about as high as 'Chandler', 'Douglas' or 'Parker' but not as high as for 'Pajaro' as measured by the Loeffler and Ponting method (1942, J. Indust. and Engin. Chem. 14:846). Soluble solids measurements fluctuate well within the range of the comparision cultivars. The flavor of 'Oso' is very good, mild sub-acid, somewhat less sharp than that of 'Chandler'. The fruit is recommended for fresh market and processing. 'Oso' is of interest for both winter and summer planting in California and should be tried in all areas.

We claim:

1. The new distinct variety of strawberry plant herein described and illustrated and identified by the characteristics enumerated above together with the parts thereof.

* * * * *